US00PP33095P2

(12) United States Plant Patent
Simon et al.

(10) Patent No.: US PP33,095 P2
(45) Date of Patent: May 25, 2021

(54) OREGANO PLANT NAMED 'PIERRE'

(50) Latin Name: ***Origanum vulgare* cultivar**
Varietal Denomination: Pierre

(71) Applicant: Rutgers, The State University of New Jersey, New Brunswick, NJ (US)

(72) Inventors: James E. Simon, Princeton, NJ (US); William Reichert, Geneva, IL (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/873,160

(22) Filed: Feb. 13, 2020

(51) Int. Cl.
*A01H 5/12* (2018.01)
*A01H 6/50* (2018.01)

(52) U.S. Cl.
USPC ..... Plt./258
CPC ..... *A01H 6/50* (2018.05)

(58) Field of Classification Search
USPC ..... Plt./258
CPC ..... A01H 6/50
See application file for complete search history.

(56) References Cited

PUBLICATIONS

Shen et al., "LC-MS method for the simultaneous quantitation of the anti-inflammatory constituents in oregano (*Origanum* species)," *J. Agric. Food Chem.*, 58:7119-7125, 2010.

*Primary Examiner* — Anne Marie Grunberg
(74) *Attorney, Agent, or Firm* — Klarquist Sparkman, LLP

(57) ABSTRACT

A new and distinct *Origanum vulgare* plant named 'Pierre' is disclosed, characterized by very high essential oil content, high carvacrol content, no flowering, broad plant width, and about 16 weeks to maturity.

1 Drawing Sheet

STATEMENT REGARDING FEDERALLY SPONSORED RESEARCH OR DEVELOPMENT

This research was supported by NIFA USDA through the New Jersey Agriculture Experiment Station under HATCH project Nos. NJ12131 and NJ12158.

Latin name of the genus and species of the plant claimed: *Origanum vulgare* cultivar.

Variety denomination: 'Pierre'.

BACKGROUND

The present disclosure comprises a new and distinct variety of *Origanum*, botanically known as *Origanum vulgare* and hereinafter referred to by the name 'Pierre'.

Oregano (*Origanum* spp., Fam. Lamiaceae) is a popular perennial aromatic herb native to Eurasia, primarily the Mediterranean region, which has a long history of established use as being the required spice in certain foods (Kintzios, S. E., Oregano: the genera *Origanum* and *Lippia*. Taylor and Francis, New York, N.Y., 2002). *Origanum* species are characterized by having ascending square stems with simple opposite leaves producing essential oils (Shafiee-Hajiabad et al., Comparative investigation about the trichome morphology of common oregano (*Origanum vulgare* L. subsp. *vulgare*) and Greek oregano (*Origanum vulgare* L. subsp. *hirtum*). J.Appl. Res. Med. Aromatic Plants. 1:50-58, 2014; Simpson, Plant systematics. Academic Press, Burlington, Mass., 2010). The inflorescence consists of a lateral cyme with flowers in verticillasters (Padulosi, The International Plant Genetic Resources Institute. 1996. Proc. Oregano Workshop, Valenzano, 8-12 May 1996; Simpson, Plant systematics. Academic Press, Burlington, Mass., 2010). Oregano's widely recognized culinary applications stem mainly from its leading characteristic volatile compound carvacrol (chemical name: 2-methyl-5-propan-2-ylphenol), which is the major constituent of Greek oregano essential oil and is responsible for its characteristic aroma (Padulosi, The International Plant Genetic Resources Institute. 1996. Proc. Oregano Workshop, Valenzano, 8-12 May 1996). Carvacrol and other aromatic compounds, such as thymol, p-cymene, and γ-terpinene, comprise the essential oil of oregano and are synthesized in peltate glandular trichomes on the leaf epidermis Shafiee-Hajiabad et al., Comparative investigation about the trichome morphology of Common oregano (*Origanum vulgare* L. subsp. *vulgare*) and Greek oregano (*Origanum vulgare* L. subsp. *hirtum*). J.Appl. Res. Med. Aromatic Plants. 1:50-58, 2014; Vokou et al., Geographic variation of Greek oregano (*Origanum vulgare* ssp. *hirtum*) essential oils. Biochemical Systematics Ecol. 21:287-295, 1993).

The production of seasonings, sauces, and condiments in the United States is a billion-dollar industry (Stivaros, IBISWorld Industry Report 31194 Seasoning, Sauce and Condiment Production in the US. IBISWorld. 1-32, 2017). Supermarket revenue represents over 30% of that market, illustrating the demand consumers have toward fresh, aromatic foods (Stivaros, IBISWorld Industry Report 31194 Seasoning, Sauce and Condiment Production in the US. IBISWorld. 1-32, 2017). Prior to the introduction of hops, oregano was used to flavor ale and beer (Kintzios, S. E., Oregano: the genera *Origanum* and *Lippia*. Taylor and Francis, New York, N.Y., 2002). Oregano is economically significant for several reasons, including for use in salads, ethnic cuisines, and as a flavoring in pizza and meats. Oregano is also utilized as a spice in commercial baking (Özcan et al., The use of the oregano (*Origanum vulgare* L.) essential oil and hydrosol in green olive fermentation. Brazilian Archives Biol. Technol. 51:601-605, 2008). Oregano has also gained notoriety for agricultural application as a feed additive, as carvacrol reduces both pathogens and odor in swine waste, while simultaneously improving feed palatability and metabolic regulation in poultry and other livestock (Faltys and Lechtenberg, Livestock and Poultry Feed Additive Composition. US 20070104765, 2007; Varel, Carvacrol and thymol reduce swine waste odor and pathogens: stability of oils. Current Microbiol. 44:38-43, 2002). Growing concern over antibiotic-resistant bacteria has prompted a response by commercial poultry companies to focus on finding alternative means of achieving healthy animal populations (Zou et al., Oregano essential oil improves intestinal morphology and expression of tight junction proteins associated with modulation of selected intestinal bacteria and immune status in a pig model. BioMed Res. Intl, 2016). Broad advertising has included adding oregano essential oil to drinking water for chickens, highlighting its nutraceutical properties (Perdue Farms, "OregaYES." Perdue Farms, Producer, perdue.com/perdueway/no-antibiotics/, 2016). Carvacrol is also utilized in the food industry as an antibacterial agent to preserve foods and prevent the colonization of harmful pathogens, further demonstrating oregano's economic potential (Jouki et al., Effect of quince seed mucilage edible films incorporated with oregano or thyme essential oil on shelf life extension of refrigerated rainbow trout fillets. Intl. J. Food Microbiol. 174:88-97, 2014; Martucci et al., Oregano and lavender essential oils as antioxidant and antimicrobial additives of biogenic gelatin films. Ind. Crops Prod. 71:205-213, 2014; Skandamis and Nychas, Effect of oregano essential oil on microbiological and physicochemical attributes of minced meat stored in air and modified atmospheres. J. Appl. Microbiol. 91:1011-1022, 2001).

Oregano's essential oil possesses numerous medicinal properties important to human health. Oil of oregano is used as an alternative to synthetic antioxidants that are commonly used in foods, such as butylated hydroxytoluene (BHT) and other natural sources, for example, α-tocopherol (Chen et al., Effects of synthetic antioxidants (BHA, BHT and PG) on the mutagenicity of IQ-like compounds. Food Chem. 43:177-183, 1992; Kulisic et al., Use of different methods for testing antioxidative activity of oregano essential oil. Food Chem. 85:633-640, 2004). Oregano and other members of the Lamiaceae family, such as basil, peppermint, and thyme, effectively inhibit lipid peroxidation in oils and fatty foods, further validating the anti-oxidant capabilities of this family (Yanishlieva et al., Natural antioxidants from herbs and spices. European J. Lipid Sci. Technol. 108:776-793, 2006). Volatiles from oregano essential oil inhibit pathologically relevant fungi, bacteria, and enteric parasites, including cariogenic pathogens, demonstrating utility for dental products (Bothelo et al., Antimicrobial activity of the essential oil from *Lippia sidoides*, carvacrol and thymol against oral pathogens. Brazilian J. Med. Biol. Res. 40:349-356, 2018; Force et al., Inhibition of enteric parasites by emulsified oil of oregano in vivo. Phytotherapy Res. 14:213-214, 2000). In a separate study, the essential oils of six different plants were comparatively tested for anti-microbial activity against 25 pathogens, in which oregano essential oil exhibited the second widest spectrum of activity (Dorman and Deans, Antimicrobial agents from plants: antibacterial activity of plant volatile oils. J. Appl. Microbiol. 88:308-316, 2000). Carvacrol, one of the more important essential oil constituents relative to aroma, flavor, and bioactivity, exhibits the lowest minimum inhibitory concentration against MRSA and MRSE strains (Nostro et al., Susceptibility of methicillin-resistant staphylococci to oregano essential oil, carvacrol and thymol. FEMS Microbiol. Lett. 230:191-195, 2004). The antioxidant and antimicrobial activity of aromatic herbs can be attributed to the hydroxyl groups in their chemical structures; carvacrol contains a free hydroxyl group (Kulisic et al., Use of different methods for testing antioxidative activity of oregano essential oil. Food Chem. 85:633-640, 2004). In addition, carvacrol's hydrophobicity provides a delocalized system that facilitates proton exchange, influencing carvacrol's antimicrobial properties (Ben Arfa et al., Antimicrobial activity of carvacrol related to its chemical structure. Lett. Appl. Microbiol. 43:149-154, 2006; Ultee et al., The phenolic hydroxyl group of carvacrol is essential for action against the food-borne pathogen *Bacillus cereus*. Appl. Environ. Microbiol. 68:1561-1568, 2002).

Oregano, as do other members of Lamiaceae, accumulates non-volatile bioactive compounds. For example, polyphenols are produced by plants throughout the kingdom and contain antioxidant activity due to their structure (Borrelli and Izzo, The plant kingdom as a source of anti-ulcer remedies. Phytotherapy Res. 14:581-591, 2000; Laghari et al., Determination of free phenolic acids and antioxidant activity of methanolic extracts obtained from fruits and leaves of *Chenopodium album*. Food Chem. 126:1850-1855, 2011). In members of the Lamiaceae family, apigenin, luteolin, and numerous other flavonoids and phenolic acids, have been identified that are medicinally bioactive for myriad medical disorders (Fecka and Turek, Determination of water-soluble polyphenolic compounds in commercial herbal teas from Lamiaceae: peppermint, melissa, and sage. J. Agr. Food Chem. 55:10908-10917, 2007). Local recipes around the world utilize herbs with radical scavenging capabilities in physiologically relevant amounts (Khomdram and Singh, Polyphenolic compounds and free radical scavenging activity in eight Lamiaceae herbs of Manipur. Notulae Scientia Biologicae. 3:108, 2011; Wong et al., Antioxidation and cytotoxic activities of selected medicinal herbs used in Malaysia. J. Med. Plants Res. 6:3169-3175, 2012). When rosmarinic, oleanic, and ursolic acids were isolated from several Greek oreganos, the compounds inhibited iNOS and COX-2 expression, signifying their ability to reduce inflammation by regulating this pathway, similar to carvacrol (Landa et al., In vitro anti-inflammatory activity of carvacrol: Inhibitory effect on COX-2 catalyzed prostaglandin E 2 biosynthesisb. Archives Pharmacal Res. 32:75-78, 2009; Shen at al., LC-MS method for the simultaneous quantitation of the anti-inflammatory constituents in oregano (*Origanum* species). J. Agr. Food Chem. 58:7119-7125, 2010).

SUMMARY

The goal of the oregano selection and crop improvement project was to select and develop a uniform *O. vulgare* plant with good field performance in the Mid-Atlantic region that grows upright to be suitable for mechanical harvest. The desired plant needs to accumulate high amounts essential oil and carvacrol yields as well as rosmarinic, oleanic, and ursolic acids for applications in the food, nutraceutical, and cosmetic industries.

Following extensive multi-year evaluations under different environments, two single plant selections, referred to as 'Pierre' and 'Eli', were specifically developed for the desired economic phenotypic characteristics that confer a significant advantage over the current commercial alternatives. 'Pierre' and 'Eli' are asexually propagated oregano cultivars that provide an alternative to the presently available *O. vulgare* sources for increased production of biomass (fresh and dried spice markets), essential oil (for flavorings and infused products), and carvacrol yields (for pharmaceutical and industrial purposes). The cultivars 'Pierre' and 'Eli' differ largely by their production and time of maturity/flowering, respectively, while still maintaining high carvacrol yields and from other studies, high concentrations of the anti-inflammatory compounds, rosmarinic, oleanic and ursolic acids as demonstrated by a previous study investigating these genetics (Shen et al. LC-MS method for the simultaneous quantitation of the anti-inflammatory constituents in oregano (*Origanum* species). J. Agr. Food Chem. 58:7119-7125, 2010).

The oregano selection and crop improvement project began in 2002 with procurement of commercially available oregano seed from a variety of commercial suppliers and the USDA Germplasm Bank. An initial prescreen subjected oregano seedlings to high environmental pressures of high winds, intense heat, and drought in 2003, where approximately 7,000 oregano plants that were originally sourced from various USDA accessions (AMES 1682, AMES 1684, AMES 1685, PL 326546, PL 440579, PL 440580) and commercial seeds were first grown in a controlled greenhouse in New Brunswick, N.J., in a randomized manner (one plant/pot) were the oregano's were allowed to grow. Some earlier flowering lines were cut back so that the plants from all the accessions and seed sources were forced to flower at the same time, cross-pollinated, with seeds then collected when mature. The collected mixed seeds were then grown and transplanted into a single field in Coolidge, Ariz., with sprinkler irrigation, and allowed to cross-pollinate. The resulting new oregano plants varied widely in maturity and phenotype, and most died due to the heat and high winds. The remaining plants were evaluated, and the most promising plants based on field performance (e.g., growth, vigor, absence of stress symptoms in the field) under the above conditions were selected for further evaluation. Four-hundred and fifty of the most promising new plants that met the preselected desirable phenotypic characteristics were manually removed from the soil (with roots) and shipped from Arizona to New Brunswick, N.J., where they were grown in a greenhouse. Vegetative clones were made from each of the 450 selected plants and evaluated under greenhouse conditions, in which 142 single plant selections (SPS) were maintained, which exhibited the desired phenotypic characteristics, including height and dry weight.

This application is directed to the 'Pierre' variety. The parents of 'Pierre' are unknown. 'Pierre' is an asexually propagated oregano cultivar that provides an alternative to the presently available *O. vulgare* sources for increased production of biomass (fresh and dried spice markets), essential oil (for flavorings and infused products), and carvacrol yields (for pharmaceutical and industrial purposes). The new variety 'Pierre' has been reproduced only by asexual propagation (vegetative propagation). Each of the progeny exhibits identical characteristics to the original plant. Asexual propagation by vegetative propagation as done in New Brunswick, N.J., shows that the foregoing characteristics and distinctions come true to form and are established and transmitted through succeeding propagations. The present invention has not been evaluated under all possible environmental conditions. The phenotype may vary with variations in environment without a change in the genotype of the plant.

The 'Pierre' variety is distinguished from other oregano varieties by high carvacrol content, lacks flowering, broad plant width, and about 16 weeks to maturity.

'Pierre' plants are uniform in production of biomass, essential oil, and carvacrol. They include opposite, short stalked, and dark green (RHS color Nos. 142C, 143D, and 144D ovate leaves with acute tips and entire edges (Tables 1 and 2, FIG. 1). This variety does not flower the entire growing season, but grows laterally on the plastic mulch rather than producing vertical flowers. These plants can be harvested 14 weeks after planting, at which time the plants are 15.8 cm tall, 69.2 cm wide, with leaf lengths and widths 1.9 cm and 1.6 cm, respectively, under the 2016 environmental conditions below. 'Pierre' produces 127.1 g of dry weight per plant and 2.0 g of essential oil per plant. The carvacrol concentration is 68.50% (Table 2, FIG. 2) of the total essential oil and a plant will yield 1.3 g of carvacrol per plant. 'Pierre' has 2.5 mg/g of gallic acid equivalents in its plant tissue or 327.9 mg per plant.

The 2016 environmental conditions include field trials and evaluating the performance of three selected clonal lines and three cloned commercial lines. The three commercial lines were Greek oregano from the Territorial Seed Company (Lot # HR1265/P) Cottage Grove, Oreg.; Greek oregano from the Park Seed Company (Lot # SD14120003) Hodges, S.C.; and Italian oregano from Franchi Sementi (Lot # 285/XV) Lawrence, Kans. (referred to herein as OST, OSP, and OSI, respectively). A randomized complete block trial with three replications was performed, in which each oregano line was evaluated for morphological characteristics, biomass, essential oil yields, and carvacrol concentration. Clones for each oregano line were produced by vegetatively propagating the selected plants at the terminal nodes and dipping them in Hormodin 2, 0.3% indole-3-butyric acid (IBA) to induce root formation; the clones were then placed in a mist house until roots developed until roots developed. Clones were generated from the commercial lines by sowing the commercial seeds and randomly taking cuttings from the seeded populations of each commercial seed supplier, similar to cloning the Rutgers breeding lines, to ensure a uniform comparison between all entries. Once the plants matured into healthy, four-node cuttings, they were transplanted to the field. The field plots were prepared on silt loam well drained soil with a pH of 5.5-6.5. Land preparation included disc-plowing then leveling the soil, where raised beds were mechanically prepared, followed by simultaneous placement of drip irrigation under plastic mulch. The land was irrigated as needed and fertilized at 900 lbs/acre of 15-15-15. In the randomized block trial, seven plants were planted for each of the six oregano entries per block with plants in single rows spaced 46 cm apart within the plots and rows spaced 247 cm apart.

Figure 1:
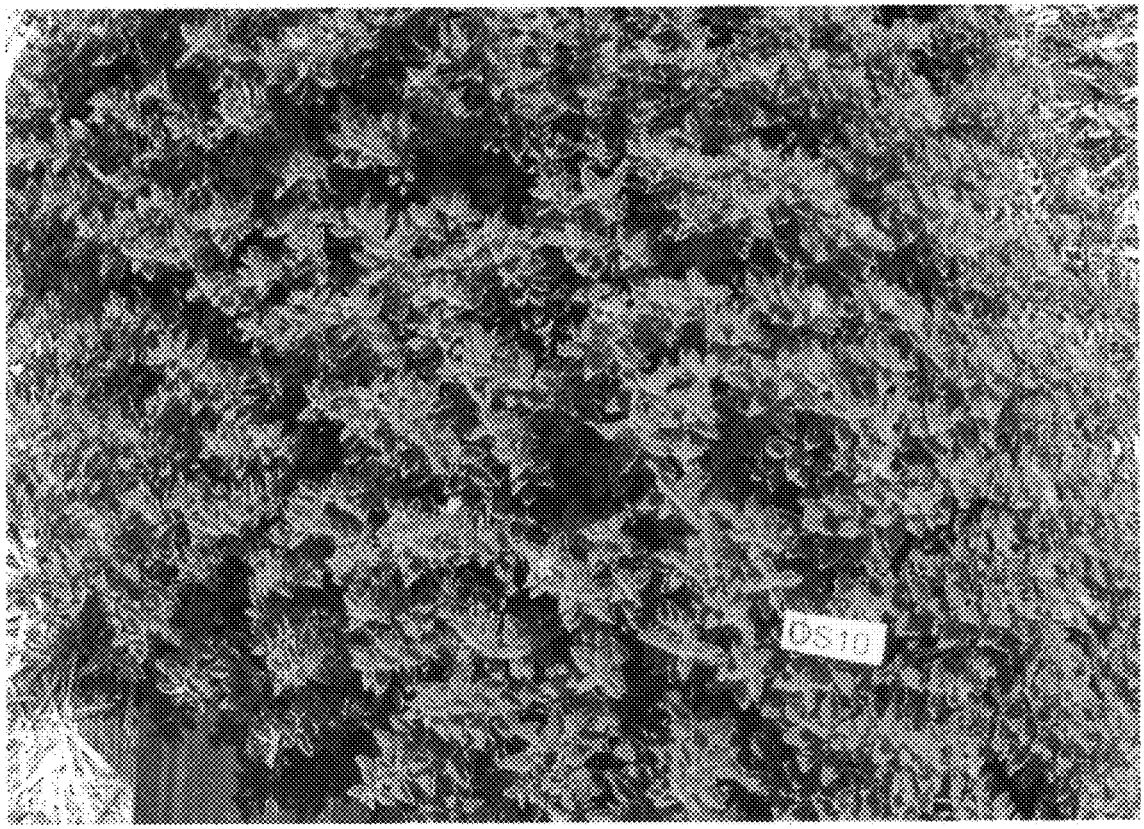
FIG. 1 shows a representative 'Pierre' plant.

The color photograph shows typical specimens of 'Pierre' and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED BOTANICAL DESCRIPTION

The following detailed description of the 'Pierre' variety is provided. The 'Pierre' plants have been observed growing in a cultivated area in Coolidge, Ariz. and New Brunswick, N.J. The observed oregano plants were one year old and growing in Pittstown, N.J. The new variety has not been evaluated under all possible environmental conditions. Certain characteristics of this variety, such as growth and color, may change with changing environmental conditions (e.g., light, temperature, moisture, nutrient availability, or other factors). The color descriptions are all based on *The Royal Horticultural Society Colour Chart,* 5$^{th}$ edition, 2007.

Scientific Name: *Origanum vulgare*

COMPARISON TO OTHER VARIETIES

Of the six new lines evaluated, the 'Pierre' variety demonstrated superior productivity in biomass, essential oil, and carvacrol yields (Table 1). The lines did not differ significantly in insect and disease damage and had green or dark green leaves, and the lines that developed flowers had white flowers. However, the Italian oregano line developed purple flowers. The 'Pierre' plants were significantly shorter than the Italian oregano, the tallest line in the field. The 'Pierre' plants were significantly wider than the four other lines ('Eli', OS37, OSI, and OSP) and were not significantly different than OST. The Greek oreganos were not statistically different in leaf length, and the Italians oregano had significantly larger leaves than the Greek oreganos. The leaves of the 'Pierre' variety had the largest width of all lines and were 6% larger than the closest commercial line. The 'Pierre' line had significantly higher biomass yields than any of the other oregano lines with a 10% improvement over the closest commercial line. The 'Pierre' variety had significantly higher essential oil yields than any of the other oregano lines. 'Pierre' had a higher overall concentration of carvacrol than the commercial lines, and the yield of carvacrol was highest in the 'Pierre' with about 54% more carvacrol per plant when compared to the closest commercial oregano evaluated (Table 2). The 'Pierre' line produced polyphenols significantly higher than the two commercial Greek Oregano's (OSP and OST) (Table 1).

Chemical profiling of the oregano essential oil via GC/MS showed that the Greek oreganos' essential oil profiles were dominated by carvacrol production (~70% of the essential oil), while the Italian oregano produced much lower concentrations. The Italian oregano plants were richer in other aroma volatiles, such as thujene, germacrene, spathulenol, and caryophyllene oxide, which were not present in the Greek oreganos. The results of a Folin-Ciocalteu assay showed that the 'Pierre' plants had medicinally relevant concentrations of phenols within the leaves of the plants. The total phenolic content for the *O. vulgare* lines was much higher than previously reported and within the range of other commonly consumed foods and reported Lamiaceae species (Wojdyło et al., Antioxidant activity and phenolic compounds in 32 selected herbs. Food Chem. 105:940-949, 2007; Wu et al., Lipophilic and hydrophilic antioxidant capacities of common foods in the United States. J. Agr. Food Chem. 52:4026-4037, 2004). These phenols contribute to the antioxidant and anti-inflammatory activity commonly reported within this family (Shen et al., LC-MS method for the simultaneous quantitation of the anti-inflammatory constituents in oregano (*Origanum* species). J. Agr. Food Chem. 58:7119-7125, 2010). The 'Pierre' plants produce a traditional aroma with increased total phenols compared with other *O. vulgare* commercial alternatives.

The commercial oreganos exhibited substantial variation in biomass, carvacrol concentration, and carvacrol yields; thus, uniform production from these lines was more challenging. 'Pierre' provides more reliably uniform oregano biomass and essential oil yields with more carvacrol. 'Pierre' also produced significantly higher yields and lower standard deviations of such characteristics compared with other commercial lines. 'Pierre' is an excellent source of oregano essential oil properties, carvacrol, and their medicinally bioactive polyphenols, while still providing aesthetically attractive edible oreganos for landscape and home gardens.

Plant:
- *Form.*—Spreading.
- *Habit.*—Upright.
- *Height* (*from the soil*).—14.1 cm-17.5 cm.
- *Width* (*plant diameter*).—64.3 cm-74.1 cm.
- *Stalk.*—short.

Stem:
- *Thickness.*—1.6 mm.
- *Distribution of leaves on the stem.*—From the base to the growing tip.

Branches:
- *Description of the lateral branches.*—Absent.
- *Branching habit.*—Absent.
- *Number of primary branches.*—30-50.
- *Number of lateral branches per primary branch.*—0.
- *Branch length.*—20-40 cm; avg 32 cm range.
- *Primary branch diameter.*—Stem diameter 1.6 mm.
- *Internode length.*—10 mm between internode.
- *Degree of lateral branches from the basil branches.*—Absent.
- *Texture of the branches* (*upper and lower sides*).—Smooth.
- *Luster of the branches* (*upper and lower sides*).—Absent.

Propagation:
- *Type.*—Cuttings (4-node).
- *Time to initiate roots.*—Any time of year, but better results are observed when the plants are actively growing.
- *Time to produce a rooted cutting.*—One week to 2 weeks.
- *Root habit.*—Fibrous.
- *Root description.*—White with many small rootlets and medium rooting depth.

Leaves:
- *Arrangement.*—Opposite.
- *Shape.*—Ovate.
- *Length.*—1.7 cm-2.1 cm.
- *Width.*—1.4 cm-1.8 cm.
- *Apex.*—Acute.
- *Margin.*—Entire.

*Prominence of leaf veins on the lower side of leaves.*—Present.

*Leaf variegation.*—Present or absent? Absent.

*Leaf blistering.*—Absent.

*Color pattern of the leaf.*—Dark Green.

*Leaf blade profile in the cross-section.*—Standard central vein.

*Leaf base shape.*—Rounded.

*Texture of the leaves (upper and lower sides).*—Smooth.

*Luster of the leaves (upper and lower sides).* Absent.

Productivity:

*Dry weight.*—121.6 g/plant-132.6 g/plant.

*Essential oil.*—1.90 g/plant-2.12 g/plant.

*Carvacrol.*—67.89%-69.11% essential oil; 1.30 g/plant-1.44 g/plant.

*Gallic acid.*—2.26 mg/g-2.90 mg/g.

Flowers and seeds: Flowers and seeds have not been observed to date.

Disease and insect resistance: No notable insect or disease damage was observed in the oregano varieties grown under the conditions disclosed herein. However, rust has been observed on the leaves of oregano plants grown under other conditions.

CHARACTERISTICS OF THE OREGANO PLANTS

The vegetative clones disclosed herein were evaluated under greenhouse conditions, where 142 single plant selections (SPS) exhibiting the desired phenotypic characteristics, including height and dry weight, were maintained. From the 142 SPS, each were harvested at time of initial flowering and then dried at 37° C. Each of the dried SPS samples (leaves and flower tops) were then hydrodistilled, and the essential oil yield calculated based upon dried weight (Reichert et al., 2016). The results indicate that 72 plants accumulated the highest amounts of essential oil. The essential oil composition was then analyzed using GC/MS analysis (Reichert et al., 'CR9': A New Highly Aromatic Catnip Nepeta cataria L. Cultivar Rich in Z, E-Nepetalactone. HortScience. 51:588-591, 2016). Chemically profiling the essential oils identified three lines of interest, OS10 ('Pierre'), OS14, and OS37 ('Eli'), which showed significantly higher levels of carvacrol. In three subsequent years (2010, 2011, and 2012), each of these three lines were clonally evaluated in randomized complete block design field trials in Pittstown, N.J. (longitude: 40.557762, latitude: −74.960574) to ensure minimal environmental influence on the variation in the production of essential oil and carvacrol yields.

The plants were evaluated (Tables 1 and 2) and harvested on the same day for the entire study, 14 weeks after transplantation, at which time the entire plot was harvested and all plants within each plot were bulked together and dried using a walk-in forced-air commercial Powell Tobacco dryer, converted for drying herbs and botanicals at 37° C. The morphological characteristics that were recorded include plant height, plant width, leaf length, leaf width, uniformity, insect and disease damage, leaf color, flower color, flowering time, and flowering percent. Plant height was measured from the soil level to the flowers, down the center of the plant. Plant width was determined by measuring the diameter of the plant. Leaf length was the measurement from the tip of the leaf to the beginning of the petiole on the side that connects to the leaf. The width of the leaf was measured at the basal portion of the leaf at the largest diameter. The leaf and flower color were determined by visually inspecting the plant. Uniformity was determined by visually inspecting the plot and giving them a rating on a scale of 1-5, 5 signifying that the population is uniform. Insect and disease damage were assessed by visually inspecting the plot for damage and rating the damage on a scale of 1-5, 5 signifying high amounts of damage. Flowering time was determined by visually identifying and taking the earliest flowering oregano line, defining that as an early flowering line and compared all other oregano lines to it bi-weekly. Flowering percent was determined by identifying the number of plants within a plot that were flowering at the time of harvest. Dry weight was recorded after the plant moisture was removed using an on-site dryer. Essential oil yield was then determined by hydro-distilling the above ground biomass of the plant. A 2 L round bottom flask was used for the distilling 30 g of dry plant matter, and a Clevenger-type trap was used to collect the essential oil. Yield was calculated as a percent of dry mass (gram of essential oil/30 g above ground biomass). Quantification of the compounds within the essential oils was performed by gas chromatography, and mass spectrometry was used for supplemental identification of the compounds. The total phenol concentration was determined using the Folin-Ciocalteu assay; the phenol concentration is expressed as gallic acid equivalents (GAE).

Tables 1 & 2: Morphological and essential oil characteristics of the new oregano 'Pierre' compared to commercial oregano varieties, 2016[Z].

TABLE 1

| Line | Leaf Color | Flower Color | Flowering Time | Flower % |
|---|---|---|---|---|
| Pierre | Dark Green | N/A | Never | 0% ± 0 C[Y] |
| Eli | Green | White | Late | 100% ± 0 A |
| OS14 | Dark Green | White | Early | 100% ± 0 A |
| OSI | Light Green | Purple | Early | 86% ± 14 A |
| OSP | Green | White | Late | 42% ± 28 B |
| OST | Dark Green | White | Late | 5% ± 8 C |

| Line | Uniformity (1-5) | I/D Damage (1-5) | Height (cm) | Plant Width (cm) |
|---|---|---|---|---|
| Pierre | 5.0 ± 0.0 A | 1.0 ± 0.0 A | 15.8 ± 1.7 CD | 69.2 ± 4.9 A |
| Eli | 4.1 ± 0.3 B | 1.0 ± 0.0 A | 18.1 ± 3.4 C | 56.5 ± 8.6 B |
| OS14 | 3.4 ± 0.4 D | 1.1 ± 0.3 A | 17.8 ± 2.9 C | 39.0 ± 5.6 C |
| OSI | 3.3 ± 0.3 D | 1.1 ± 0.3 A | 24.5 ± 3.4 A | 56.4 ± 15.4 B |
| OSP | 3.8 ± 0.3 C | 1.1 ± 0.3 A | 20.8 ± 7.8 B | 63.5 ± 27.3 AB |
| OST | 4.8 ± 0.3 A | 1.1 ± 0.3 A | 14.0 ± 4.1 D | 70.5 ± 11.5 A |

| Line | Leaf Length (cm) | Leaf Width (cm) | Dry Weight (g)/Plant |
|---|---|---|---|
| Pierre | 1.9 ± 0.2 B | 1.6 ± 0.2 A | 127.1 ± 5.5 A |
| Eli | 1.9 ± 0.2 B | 1.4 ± 0.2 BC | 94.1 ± 10.0 BC |
| OS14 | 1.9 ± 0.2 B | 1.3 ± 0.2 C | 43.6 ± 5.8 D |
| OSI | 2.3 ± 0.7 A | 1.5 ± 0.2 BC | 114.4 ± 17.9 AB |
| OSP | 2.0 ± 0.3 B | 1.4 ± 0.2 BC | 76.2 ± 20.2 C |
| OST | 1.9 ± 0.1 B | 1.5 ± 0.2 AB | 115.1 ± 10.4 AB |

TABLE 2

| Line | Essential Oil Yield (g)/Plant | Carvacrol Concentration (%) | Carvacrol yield (g)/plant | Gallic Acid Equivalents (mg/g) |
|---|---|---|---|---|
| Pierre | 2.01 ± 0.11 A | 68.50 ± 0.61 C | 1.37 ± 0.07 A | 2.58 ± 0.32 AB |
| Eli | 1.62 ± 0.47 AB | 72.77 ± 0.68 A | 1.18 ± 0.35 AB | 2.47 ± 0.3 BC |
| OS14 | 0.79 ± 0.23 CD | 71.76 ± 1.12 B | 0.57 ± 0.15 BC | 2.82 ± 0.15 A |
| OSI | 0.14 ± 0.01 D | 6.37 ± 4.94 F | <0.1 ± 0.01 C | 2.89 ± 0.06 A |
| OSP | 0.95 ± 0.46 BC | 61.50 ± 15.57 D | 0.62 ± 0.37 B | 2.37 ± 0.08 BC |
| OST | 0.92 ± 0.36 BC | 60.98 ± 17.94 E | 0.6 ± 0.4 B | 2.20 ± 0.12 C |

[Z]'Pierre' = *Origanum vulgare* cultivar; 'Eli' = *Origanum vulgare* cultivar; OS14 = line; OSI = Franchi Sementi, Lawrence, KS; OSP = Park Seed Company, Hodges, SC; OST = Territorial Seed Company, Cottage Grove, OR.
[Y]Values within columns followed by the different letters are significantly different according to Duncan's test at P ≤ 0.05.

ESSENTIAL OIL IDENTIFICATION AND MEASUREMENT

Figure 2:
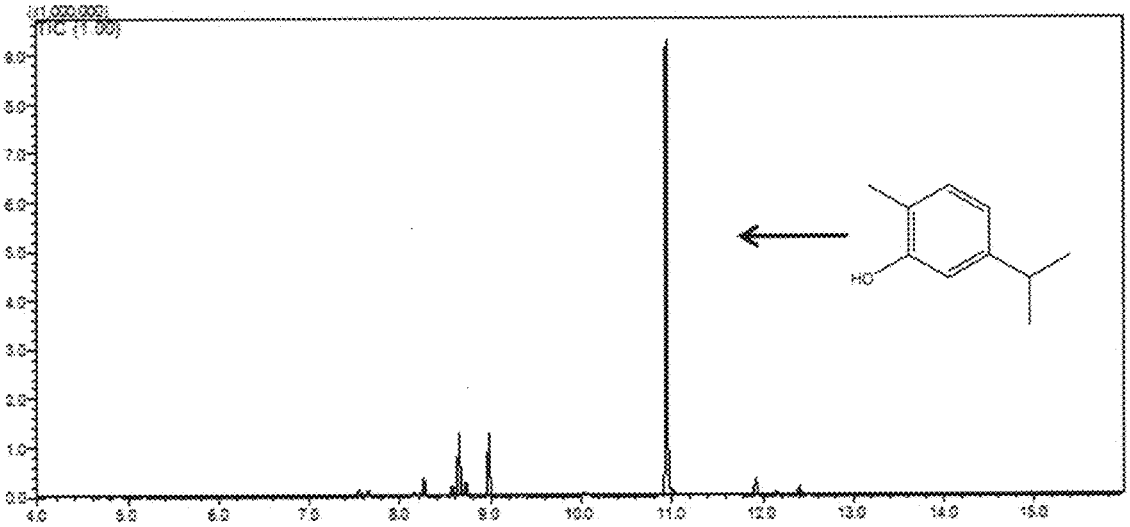
FIG. 2 shows a representative chromatogram of the essential oil from oregano 'Pierre' (also referred to as OS10), illustrating the carvacrol peak.

Essential oil samples were analyzed by extracting 5 μL of pure hydrodistilled oils, which was distilled from 30 g of dry plant material, with 1.5 mL of MTBE (methyl-tert butyl ether). The samples were then dried over anhydrous sodium sulfate and centrifuged at 6 krpm. The supernatant was then transferred to a sampling vial and analyzed using GC/MS. All samples were separated using a Shimadzu Gas Chromatograph 2010 Plus on column SH-Rxi-5Sil MS heated from 35° C. with a hold of 4 min, to 250° C. with a hold of 1.25 min at 20° C./min. The injection volume for the essential oil samples was 1 μL, and the inlet temperature was 250° C. with a split of 300. A Shimadzu TQ8040 Triple-Q MS was used for compound identification with the ion source temperature set to 200° C., the interface temperature set to 250° C., the solvent cut time at 3.5 min, and the detector voltage set to 0.2 kV with a threshold of 1000. The samples were integrated using GCMS solution v4.3© Shimadzu Corporation. Individual compound ID's were determined by comparing the results with current literature and screening against the NIST05.LIB, NIST05s.LIB, W10N14.lib, and the W10N14R.lib mass spectral libraries with a >90% similarity search. An authenticated carvacrol standard was co-injected to confirm the identity of that peak in the chromatogram (FIG. 2, which shows a representative chromatogram of the essential oil from oregano 'Pierre', illustrating the carvacrol peak).

The total phenolic content of the plant was measured using the Folin-Ciocalteu reagent, also referred to as Folin's reagent, to quantitate gallic acid equivalents (Table 3). An extract was prepared by adding 25 mL of 60% methanol solution to ca. 50 mg of dried, ground oregano leaf material and then sonicating for 25 min. The extract was then transferred to a centrifuge tube and centrifuged for 3 minutes at 6 krpm, after which the supernatant was removed. The Folin's reagent was prepared by adding 2 mL of Folin's reagent to 20 mL of distilled water with a ratio of 1:10, Folin's reagent to distilled water. Once the solutions were prepared, a standard curve was generated by adding 25 ml of a 60% methanol solution to 9.2 mg of gallic acid and serially diluting to 1/512× of the original concentration. Thereafter, 40 μL of each dilution was added to 900 μL of Folin's reagent and allowed to sit for 5 min; 400 μL of the 15% sodium carbonate solution was then added, and the dilution sample was stored in the dark for 45 min, after which the absorbance was measured at 752 nm. Once the curve was generated, 900 μL of Folin's reagent was added to 40 μL of each oregano extract. The mixture was allowed to react for 5 minutes, at which time a 15% 400 μL of sodium carbonate solution was added. The sample tubes were then covered in aluminum foil and stored in the dark for 45 minutes. Thereafter, 200 μL of each sample was aliquoted into a 96-well plate, and the sample's absorbance was measured at 752 nm.

TABLE 3

Composition of the aromatic essential oil constituents from the hydrodistilled oregano essential oils showing 11 essential oil constituents that represent >90% of the overall peak area detected in the six oregano essential oil genetic lines ('Pierre' (also referred to as OS10), OS14, 'Eli' (also referred to as OS37), OST, OSP, OSI), including the retention time and peak area percentages.

| ID # | Compound Name | Rt (min) | Pierre[Z] | OS14 | Eli | OST | OSP | OSI |
|---|---|---|---|---|---|---|---|---|
| 1 | α-Thujene | 8.09 | ND[Y] | ND | ND | ND | ND | 6.17 |
| 2 | β-Myrcene | 8.26 | 2.60 | 1.48 | 2.32 | 1.12 | 1.16 | 0.79 |
| 3 | α-Terpinene | 8.57 | 1.43 | 1.52 | 1.55 | 1.45 | 1.66 | 0.51 |
| 4 | para-Cymene | 8.65 | 9.75 | 7.35 | 8.89 | 9.14 | 10.22 | 10.49 |
| 5 | γ-Terpinene | 8.98 | 10.19 | 12.95 | 8.50 | 8.74 | 10.93 | 4.99 |
| 6 | Thymol | 10.84 | ND | ND | ND | 2.18 | 5.56 | 18.56 |
| 7 | Carvacrol | 10.94 | 68.50 | 71.76 | 72.71 | 71.94 | 65.38 | 6.37 |
| 8 | (E) - Caryophyllene | 11.92 | 2.35 | 0.33 | 1.23 | 1.16 | 0.93 | 12.59 |
| 9 | Germacrene D | 12.31 | ND | ND | ND | ND | ND | 18.43 |
| 10 | Spathulenoly | 12.92 | ND | ND | ND | ND | ND | 7.35 |
| 11 | Caryophyllene oxide | 12.97 | ND | ND | ND | ND | ND | 6.21 |

[Z]'Pierre' = *Origanum vulgare* cultivar; 'Eli' = *Origanum vulgare* cultivar; OS14 = line; OSI = Franchi Sementi, Lawrence, KS; OSP = Park Seed Company, Hodges, SC; OST = Territorial Seed Company, Cottage Grove, OR.
[Y]ND: Compounds not detected in the sample

We claim:

1. A new and distinct variety of *Origanum vulgare* plant as illustrated and described.

* * * * *